United States Patent [19]
Bickel et al.

[11] 3,955,404
[45] May 11, 1976

[54] RESONANT SENSING DEVICE

[75] Inventors: Wolf Bickel; Ulrich Eichert, both of Cologne; Ludwig Niklas, Lovenich, all of Germany

[73] Assignee: Krautkramer-Branson, Incorporated, Stratford, Conn.

[22] Filed: Oct. 15, 1974

[21] Appl. No.: 514,704

[30] Foreign Application Priority Data
Nov. 15, 1973 Germany............................ 2357033

[52] U.S. Cl.................................. 73/67.2; 73/67.1
[51] Int. Cl.².......................................... G01N 29/00
[58] Field of Search ............... 73/67.2, 67.1, 67, 78, 73/81

[56] References Cited
UNITED STATES PATENTS

| | | |
|---|---|---|
| 3,153,338 | 10/1964 | Kleesattel ........................... 73/67.1 |
| 3,302,454 | 2/1967 | Kleesattel ........................... 73/67.1 |
| 3,307,393 | 3/1967 | Kessler................................ 73/67.1 |
| 3,323,352 | 6/1967 | Branson .............................. 73/67.1 |
| 3,472,063 | 10/1969 | Branson .............................. 73/67.1 |
| 3,595,069 | 7/1971 | Fowler................................. 73/67.2 |

OTHER PUBLICATIONS
*Ultrasonics*, "Ultrasonic Hardness Testing," Apr. 1966, pp. 88–91.

*Primary Examiner*—Richard C. Queisser
*Assistant Examiner*—Stephen A. Kreitman
*Attorney, Agent, or Firm*—Ervin B. Steinberg; Philip J. Feig

[57] ABSTRACT

The invention refers to a measuring circuit for determining the properties of a workpiece, particularly hardness, using the contact impedance method in which a probe resonating at an ultrasonic frequency provided with a workpiece engaging tip is utilized. The measuring circuit uses digital counters for producing a digital count which is the difference between the free-resonant frequency of the test probe and the resonant frequency of the probe when the probe is in forced contact with the workpiece. A read-only-memory (ROM) converts the difference frequency count to a hardness value, such as Vickers or Rockwell. The disclosed arrangement obviates the need for zeroizing the circuit and, hence, is self-compensating in respect to drift and thermal stability.

9 Claims, 2 Drawing Figures so that the magnetostrictive

RESONANT SENSING DEVICE

BACKGROUND OF THE INVENTION

This invention relates to a resonant sensing device used for measuring material properties as disclosed in U.S. Pat. No. 3,153,338 issued to C. Kleesattel on Oct. 20, 1964 entitled "Resonant Sensing Devices". The disclosed device comprises an elongate transducer having a workpiece engaging tip at one end, means for rendering the transducer resonant at its natural frequency of oscillation, and means for measuring and indicating the frequency shift of the transducer from its free resonant condition to the condition when the workpiece engaging tip is urged with predetermined static force into contact with the surface of a workpiece to be measured. The impedance of the workpiece, being related to the modulus of elasticity of the workpiece, loads the transducer during such contact and causes the resonant frequency of the transducer to shift to a higher value. This shift is a measure of the hardness of the workpiece and can be expressed, for instance, in units of Rockwell or Vickers.

A typical circuit for determining the frequency shift of the transducer from its unloaded to its loaded condition has been disclosed in U.S. Pat. No. 3,323,352 issued to Norman G. Branson on June 6, 1967 entitled "Control Circuit for Resonant Sensing Device". In this circuit the frequency shift of the transducer is converted by a frequency discriminator to an electrical direct current voltage signal whose amplitude is indicated by the deflection of a pointer on a conventional current measuring instrument. Using this type of measuring circuit two adjustable means are necessary for adjusting respectively the zero point setting and the scaling.

Due to the relatively small value of the frequency shift which is to be determined, very exacting requirements with respect to the stability of the discriminating circuit and the resonant frequency range, must be met. In practice these requirements are difficult to fulfill. Therefore, calibration measurements using calibrated test specimens are required repeatedly during the measurement process, specifically to establish the zero point, see C. Kleesattel and G. M. L. Gladwell, "The Contact Impedance Meter", Ultrasonics (magazine) Illiffe Publications, London, England, July 1968, October 1968, January 1969, and January 1970.

BRIEF SUMMARY OF THE INVENTION

The present invention discloses as its principal feature a measuring circuit for determining the properties of a workpiece, particularly hardness, with a high degree of accuracy and stability using the contact impedance method, while obviating the requirement for zeroizing the circuit before and during the time in which measurements are made. Hence, measurements can be carried out without wasted time and effort.

In accordance with the present invention, the frequency of the transducer in its free resonant condition is established and the resulting value is stored in a storage means. During an ensuing time interval in which the transducer is in forced contact with a workpiece the shifted frequency of oscillation is measured and subsequently the difference between both values is derived. This difference value is transformed to a value indicative of the property of the workpiece and is displayed and/or recorded.

A specific feature of the present invention comprises an arrangement for causing the frequency measurement and the difference frequency to be fed to a forward-backward digital counter which is preset to the frequency value determined when the transducer is in its free-resonant state.

Another feature of this invention comprises the use of at least one read-only-memory (ROM) for converting a numerical value indicative of the frequency difference to a numerical value commensurate with the workpiece property.

A further significant feature of the present invention comprises an arrangement for measuring and storing a value indicative of the free natural resonant frequency of the transducer immediately preceding contact of the transducer with the workpiece.

A still further salient feature of the present invention comprises the provision of a measuring instrument which is simple to operate due to automatic zero point correction resulting from the generation of a numerical value which is the frequency difference, and the conversion of this numerical value to a value indicative of the material properties, e.g. hardness, by means of an exchangeable read-only-memory, the latter permitting connection to an easily readable digital indicator.

Further and still other features and objects of this present invention will be more clearly apparent from the following description when taken in conjunction with the accompanying drawings.

DESCRIPTION OF THE PREFERRED EMBODIMENT

Figure 1:
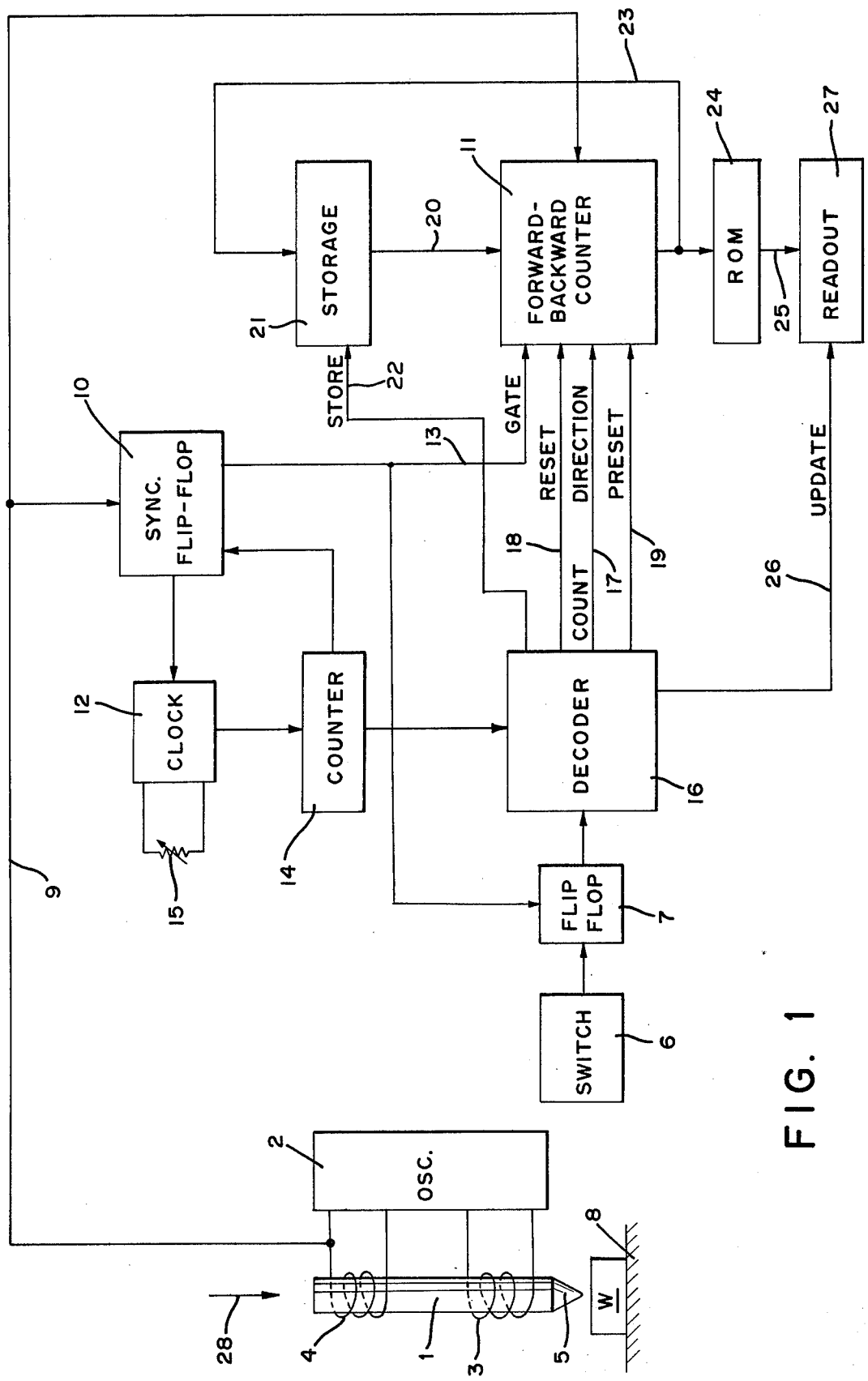
FIG. 1 is a schematic block diagram of a preferred embodiment of the invention.

Referring now to the figures and FIG. 1 in particular, a bar shaped transducer 1, made of magnetostrictive material, is rendered resonant along its longitudinal axis at its natural frequency of oscillation by means of a feedback oscillator 2 which transmits an excitation signal to an excitation coil 3 and receives a feedback signal from a feedback coil 4, both coils encircling the transducer 1. One end of the transducer 1 is fitted with a workpiece engaging tip 5 which is made of a hard substance, e.g. a diamond as used for measuring the hardness of a workpiece W in accordance with the Vickers or Rockwell hardness test method. The workpiece may be self-supporting or disposed on a support 8. The described transducer construction is substantially identical with that shown and described in the patent to Kleesattel supra, typically having a resonant frequency in the range form 20 to 100 kHz, depending upon the physical dimensions of the transducer.

A sensing means, such as a mechanical switch 6 provides a signal responsive to the condition whether the tip 5 is free or in contact with the workpiece W as the result of a force along the direction of arrow 28. This condition responsive signal provided by the switch is fed to the flip-flop 7. The switch is mechanically coupled to the protective shell (not shown) surrounding the probe. When the probe tip is free in air, the switch signal condition denotes that the tip 5 is free of contact with the workpiece or unloaded. When the shell of the probe contacts the workpiece, immediately preceding the tip 5 being in forced engagement with the workpiece, the switch condition is changed and this changed signal condition applied to flip-flop 7 denotes that the probe is shifting or has shifted to a higher frequency responsive to engagement with the workpiece. In this manner, as will be more clearly evident later, automatic temperature compensation and zeroizing is performed whenever the probe is removed from the workpiece surface.

Figure 2:
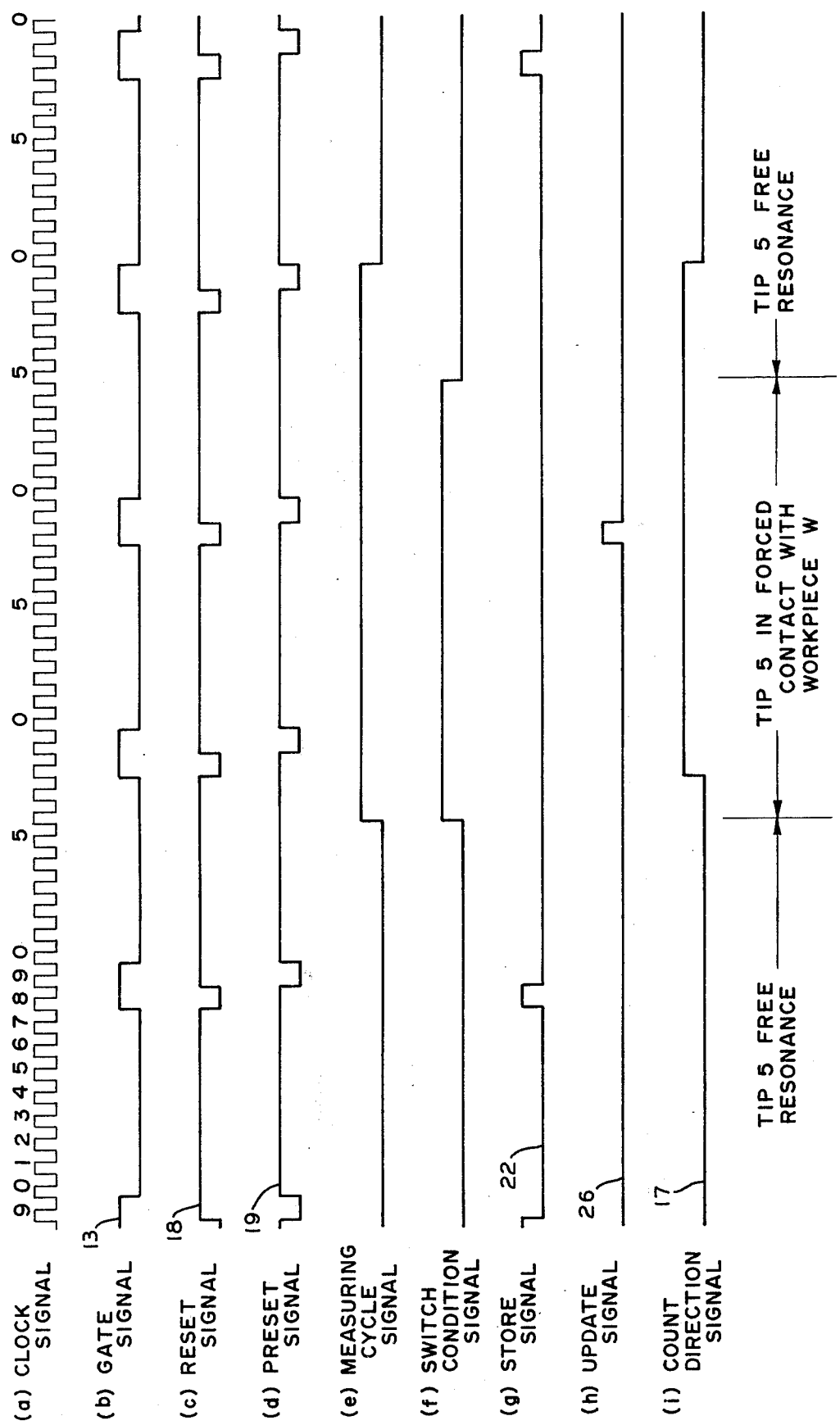
FIG. 2 is a timing diagram applicable to the embodiment per FIG. 1.

A measuring signal whose frequency is identical with the frequency of oscillation of the transducer 1 is transmitted from the feedback coil 4 via conductor 9 to the forward-backward counter 11 and to the synchronization flip-flop 10. The counter 11 counts the cycles of the measuring signal provided along conductor 9 during a predetermined time interval which is controlled by the presence of a gate signal. The gate signal, see also FIG. 2b, is provided by the synchronization flip-flop 10 to the forward-backward counter 11 via conductor 13. The receipt of the measuring signal at the synchronization flip-flop 10 causes the gate signal along conductor 13 to be in a logic level 0 state. An additional output signal from the synchronization flip-flop 10 transmitted to clock 12 starts the clock 12. The output pulses of clock 12, FIG. 2a, are conducted to counter 14. After a predetermined number of counts, for instance, after the seventh clock pulse as shown in FIG. 2, a signal is provided from the counter 14 to the synchronization flip-flop 10 to stop the gate signal from the synchronization flip-flop 10 to the forward-backward counter 11 along conductor 13. The duration of the gate signal is derived from the frequency of the clock 12. The gate signal measuring interval and the clock are started by the output signal from the synchronization flip-flop 10, and are terminated after a predetermined number of clock pulses have been counted by counter 14. The count accumulated in the forward-backward counter 11 at the end of the gate signal measuring time interval is proportional to the frequency of oscillation of the transducer 1. A calibration correction can be made by adjusting potentiometer 15, thereby varying the frequency of the clock 12 and the time at which counter 14 counts the predetermined number of pulses for providing a signal to synchronization flip-flop 10 to terminate the gate signal on conductor 13. The repetition rate of the gate signal along conductor 13 is controlled by the cyclic trigger signal from counter 14 which periodically resets the synchronization flip-flop 10.

A decoder 16 provides the system synchronization signals responsive to the count signal received from the counter 14. The count direction signal FIG. 2i, along conductor 17 is used for controlling the count direction of the forward-backward counter 11. At the end of the measuring time interval, as determined by the gate signal (conductor 13), a reset signal FIG. 2c, provided along conductor 18 to the forward-backward counter 11 resets or clears the previously accumulated count in the counter 11. A preset signal, FIG. 2d, conducted from decoder 16 to forward-backward counter 11 via conductor 19, is used to reset, via conductor 20, the forward-backward counter 11 to the count previously stored and now contained in storage means 21. A store signal, FIG. 2g, along conductor 22 from the decoder 16 to the storage means 21 causes the storage means 21 to store the output count of the forward-backward counter 11 via conductor 23.

The output of the forward-backward counter 11, besides being transmitted to the storage means 21, is transmitted also to the input address of a read only memory 24 (ROM) whose output is provided along conductor 25 to a readout means 27. An update signal, FIG. 2h, from decoder 16 along conductor 26 causes the value displayed in readout means 27 to be updated to the last measured value of the hardness of the workpiece W. The readout means 27, in a typical case, comprises a digital indicator.

DESCRIPTION OF SEQUENCE OF OPERATION

The sequence of operation of the above described embodiment will be more clearly apparent by reference also to FIG. 2. The principle of operation resides in the determination of the increase in resonant frequency of the transducer 1 between its free resonant state and its forced contact state with the workpiece. This frequency difference is a measure of the hardness of the workpiece.

The circuit is zeroized when the tip 5 is not in contact with the workpiece W and a signal indicative of the "free resonance" condition is transmitted from switch 6, FIG. 2f, to an input of flip-flop 7. The flip-flop 7 provides a signal, FIG. 2e, to decoder 16 indicative that the frequency of the free resonant transducer 1 is to be measured. The decoder 16 provides a count direction signal, FIG. 2i, along conductor 17 to the forward-backward counter 11, causing the forward-backward counter 11 to count in the backwards direction.

Responsive to the arrival of the gate signal, FIG. 2b, along conductor 13 at the forward-backward counter 11, the counter 11 counts, in the backwards direction, the free resonant frequency of the ultrasonic transducer 1. At the end of the gate signal measuring time interval, FIG. 2b, the output count of the forward-backward counter 11 is provided via conductor 23 to the input of the storage means 21. Upon receipt of the store signal from decoder 16 to storage means 21 via conductor 22, the count is stored in the storage means 21. A reset signal, conductor 18, from decoder 16 to forward-backward counter 11 clears the count in the forward-backward counter 11. This cycle of events is repeated responsive to the repetition frequency of the counter 14 and the time interval required to count a predetermined number of counts during which interval the frequency of oscillation of transducer 1 is measured.

The readout means 27, during this zeroizing time interval is inoperative, showing no hardness value indication until the tip 5 is brought into forced contact with the workpiece W.

When the tip 5 is brought in forced contact with the workpiece W, a signal from switch 6 causes the output of flip-flop 7 to change logic level states. The output of flip-flop 7 is conducted to the decoder 16 to initiate the hardness measurement cycle. A preset signal from decoder 16 along conductor 19 to the forward-backward counter 11 causes the last count stored in the storage means 21 during the preceding zeroizing cycle to be transmitted via conductor 20 to the forward-backward counter 11 for presetting the counter. The count direction signal along conductor 17 causes the forward-backward counter 11 to count forward, the opposite direction from that in the preceding zeroizing cycle.

The frequency of oscillation measured when the tip 5 is in forced engagement with the workpiece W is higher than the frequency measured when the tip 5 is exposed to air. The forward-backward counter 11 once again operates during the time interval determined by the gate signal from synchronization flip-flop 10 provided along conductor 13. The frequency difference, represented by a numerical value, or counts, is apparent at the output of the forward-backward counter 11 and is responsive to the hardness of the workpiece.

The output from the forward-backward counter 11, i.e. the difference value, is provided as the address input to the read only memory 24. A value responsive to the address is contained in the storage of the non-changeably programmed read only memory 24 in such a manner that for each frequency difference value a hardness value is indicated and is transmitted to the readout means 27. Upon transmission of an update signal from decoder 16 to the readout means 27 via conductor 26, the hardness value will be displayed and/or recorded by the readout means 27. Exchangeable or switchable memory means 24 with different programmed content make it possible to use various scales, in the case of hardness, for instance, value of Vickers or Rockwell.

The above described cycle of operation is cyclically repeated by providing the reset signal along the conductor 18 for zeroizing the forward-backward counter 11, providing the preset signal along conductor 19 for feeding the count stored during the last cycle of operation of the previous zeroizing cycle from the storage means 21 via conductor 20 to the forward-backward counter 11, and providing an update signal along conductor 26 to the readout means 27. In this manner, the frequency difference value is repetitively determined and an updated value displayed and/or recorded.

After a particular measurement has been made, the gate signal from synchronization flip-flop 10 resets flip-flop 7, and the transducer 1 with tip 5 is removed from engagement with the workpiece W and a new zero measurement (free resonant frequency) including automatic temperature compensation is made. Hence, automatic zero point measurement correction is attained fully automatically. This correction compensates for shifts of the resonance frequency of the transducer, instability of the feedback oscillator circuit, thermal effects and the like.

It will be apparent to those skilled in the art that the magnetostrictive transducer 1 shown in FIG. 1, may be replaced by piezoelectric transducer without deviating from the principle of the present invention. Such a piezoelectric transducer embodiment is shown in U.S. Pat. No. 3,472,063, issued to N. G. Branson, dated Oct. 14, 1969, entitled "Resonant Sensing Device" and in U.S. Pat. No. 3,308,476, issued to C. Kleesattel, dated Mar. 7, 1967, entitled "Resonant Sensing Devices", FIG. 5.

What is claimed is:

1. A resonant sensing device for determining the property, such as hardness, of a workpiece comprising:
   an elongate transducer adapted to be resonant and having a workpiece engaging tip at one end;
   oscillator means coupled to said transducer for rendering said transducer resonant;
   counting means coupled to said transducer for providing and storing a first value commensurate with the resonant frequency of said transducer when said tip is free of engagement with a workpiece and for providing a second value commensurate with the resonant frequency of said transducer when said tip is in forced engagement with a workpiece;
   control means coupled to said counting means responsive to said tip being in forced engagement with a workpiece for causing said counting means to be operative for providing an output value commensurate with the difference between the stored first value and the second value, and
   means for receiving said output value and transforming it to a value related to the workpiece property and indicating such property related value.

2. A resonant sensing device as set forth in claim 1, said first value and said second value being digital counts.

3. A resonant sensing device for determining the property of a workpiece comprising:
   A. an elongate transducer adapted to be resonant and having a workpiece engaging tip at one end;
   B. oscillator means coupled to said transducer for rendering and maintaining said transducer resonant and providing a signal responsive to the resonant frequency of said transducer;
   C. a forward-backward counter coupled for receiving said signal responsive to the resonant frequency of said transducer and accumulating counts responsive to said frequency;
   D. timing means coupled to said counter for causing said counter to accumulate counts responsive to said resonant frequency signal during predetermined time intervals;
   E. condition responsive means associated with said transducer for providing a first signal condition when said tip is free of engagement with the workpiece and a second signal condition when said tip is in forced engagement with the workpiece;
   F. a storage means coupled to said counter;
   G. a decoder means coupled to said condition responsive means, said timing means, said counter and said storage means for cyclically providing signals to said counter for causing said counter to accumulate said counts and responsive to said condition responsive means providing said first signal condition:
      1. causing said counter to count in a first direction;
      2. providing at end of each of said intervals a "store" signal to said storage means for causing said storage means to store the count accumulated;
      3. providing at the end of each said intervals a "reset" signal to said counter for zeroizing said counter, and responsive to said condition responsive means providing said second signal condition:
      4. causing said counter to count in a second direction which is opposite to said first direction;
      5. providing at the end of each of said intervals a reset signal to said counter for zeroizing said counter;
      6. causing the last count stored in said storage means to remain stored in said storage means and at the beginning of each of said intervals to be inserted into said counter for presetting the counter with said stored count;
      7. causing at the end of each of said intervals the difference count between said stored count and the count accumulated during the operation of the counter in said second direction to be coupled to a readout means.

4. A resonant sensing device for determining the property of a workpiece as set forth in claim 3, said decoder means causing said counter to count backward responsive to said first signal condition and to count forward responsive to said second signal condition.

5. A resonant sensing device for determining the property of a workpiece as set forth in claim 4, said readout means including a read-only-memory (ROM).

6. A resonant sensing device for determining the property of a workpiece as set forth in claim 4, and means for adjusting the duration of said intervals.

7. A resonant sensing device for determining the property of a workpiece as set forth in claim 4, said readout means indicating units of hardness.

8. A resonant sensing device for determining the property of a workpiece as set forth in claim 5, said read-only-memory being exchangeable.

9. A resonant sensing device for determining the property, such as hardness, of a workpiece comprising:
 a transducer adapted to be resonant having a workpiece engaging tip at one end thereof;
 means coupled to said transducer for rendering said transducer resonant;
 switching means disposed for providing a respective condition responsive signal denoting when said tip is free of contact with the workpiece and when the tip is in forced engagement with the workpiece;
 a forward-backward digital counter and a storage means;
 means coupled for causing said forward-backward counter to receive cylically during predetermined time intervals counts responsive to the frequency of oscillation of said transducer;
 decoder means coupled to said counter and said switching means for causing said counter to cyclically accumulate a first value of counts by counting in one direction during said predetermined time intervals responsive to said condition responsive signal denoting that said tip is free of contact with a workpiece and to cyclically store said accumulated first value of counts in said storage means, and responsive to said condition responsive signal denoting forced contact between said tip and the workpiece, causing the last-stored first value of counts cyclically at the beginning of each predetermined time interval to be inserted into said counter and said counter to cyclically accumulate a second value of counts during said time intervals by counting in the opposite direction, thereby providing the difference value between said stored first value of counts and said second value of counts, and
 means coupled to said counter for receiving said difference value of said counts and converting said value to a workpiece property related value and for providing an indication of said property related value.

* * * * *